United States Patent [19]

Kouchiwa et al.

[11] Patent Number: 4,906,647

[45] Date of Patent: Mar. 6, 1990

[54] STABILIZED PHARMACEUTICAL COMPOSITIONS

[75] Inventors: Shozo Kouchiwa, Oomiya; Masami Nemoto, Okegawa; Tetsuo Yamaguchi; Atsuro Nakazato, both of Ageo, all of Japan

[73] Assignee: Taisho Pharmaceutical Co., Ltd., Japan

[21] Appl. No.: 103,297

[22] Filed: Oct. 1, 1987

[30] Foreign Application Priority Data

Oct. 13, 1986 [JP] Japan .................. 61-241299

[51] Int. Cl.$^4$ ............................................. A61K 31/44
[52] U.S. Cl. ..................................... 514/356; 514/970
[58] Field of Search .................................. 514/356, 970

[56] References Cited

U.S. PATENT DOCUMENTS

| | | | |
|---|---|---|---|
| 4,472,411 | 9/1984 | Hatayama et al. | 514/356 |
| 4,582,840 | 4/1986 | Garthoff et al. | 514/356 |

FOREIGN PATENT DOCUMENTS

| | | |
|---|---|---|
| 42809 | 11/1985 | Australia . |
| 0159735 | 3/1985 | European Pat. Off. . |
| 0164588 | 12/1985 | European Pat. Off. . |
| 0168789 | 1/1986 | European Pat. Off. . |
| 60-89420 | 5/1985 | Japan . |

OTHER PUBLICATIONS

Patent Abstracts of Japan, vol. 10, No. 131 (C-346) [2188], 5/15/86.
Patent Abstracts of Japan, vol. 10, No. 258 (C-370) [2314], 09/4/86.

Primary Examiner—Paul Lieberman
Assistant Examiner—Christine A. Skane
Attorney, Agent, or Firm—Lorusso & Loud

[57] ABSTRACT

Stabilized solid pharmaceutical preparations in which one or more of sodium carbonate, sodium hydrogen carbonate, calcium carbonate and calcium hydrogen phosphate are incorporated in a solid composition containing a 1,4-dihydropyridine derivative as an active ingredient. The present compositions are used as an oral therapeutic agent for the circulatory system, especially as a coronary vasodilator.

5 Claims, No Drawings

STABILIZED PHARMACEUTICAL COMPOSITIONS

BACKGROUND OF THE INVENTION

1. Field of the Invention

The present invention relates to stabilized pharmaceutical compositions.

More particularly, it is concerned with stabilized therapeutic compositions for circulatory diseases containing a dihydropyridine derivative as an active ingredient.

2. Description of the Prior Art

Dihydropyridine derivatives which are an active ingredient of the compositions of the invention are disclosed in Japanese Patent Laid-Open-to-Public No. 60-89420 for preparative process and pharmacological effects in the circulatory system. However, technique for stabilizing the compounds in long-term storage has not been known.

The dihydropyridine derivatives used as the active ingredient of the invention are apt to be much decomposed in solid pharmaceutical preparation, and long-term storage of the preparation is a problem in stabilization.

It is an object of the invention to provide stabilized pharmaceutical compositions.

DETAILED DESCRIPTION OF THE INVENTION

The present invention is directed to a solid pharmaceutical composition containing as an active ingredient a 1,4-dihydropyridine derivative represented by the general formula

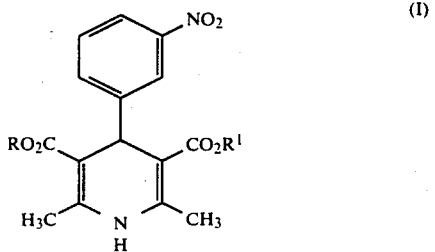

(wherein R is a n-propyl group substituted at the 2- or 3-position with a nitrato group and $R^1$ is a 2-nitratoethyl group which may be substituted with a methyl group at the 1- or 2-position) and pharmaceutical auxiliary agents and, one or more compounds selected from the group consisting of sodium carbonate, sodium hydrogen carbonate, calcium carbonate and calcium hydrogen phosphate.

It is also directed to a method for stabilizing a solid pharmaceutical composition containing as an active ingredient said 1,4-dihydropyridine derivative (I), which comprises incorporating in the composition one or more of sodium carbonate, sodium hydrogen carbonate, calcium carbonate and calcium hydrogen phosphate.

Amount of sodium carbonate, sodium hydrogen carbonate and/or calcium carbonate used in the invention is in the range from 0.01 to 20 parts by weight and preferably from 0.01 to 10 parts by weight, and that of calcium hydrogen phosphate is in the range from 0.01 to 100 parts by weight and preferably from 0.1 to 80 parts by weight all being per part by weight of the compound of the general formula (I) contained.

The stabilized compositions of the invention can be prepared by any of the conventionally employed means. For example, to said compound are added one or more of sodium carbonate, sodium hydrogen carbonate, calcium carbonate and calcium hydrogen phosphate followed by addition of pharmaceutical auxiliary agents such as excipient, lubricant and disintegrant, if needed, and a variety of pharmaceutical preparations such as powders, tablets, capsules and granules can be formed from the mixture.

To the stabilized compositions of the invention may be added lactose, corn starch and/or mannitol as the excipient that does not hurt the stability at a ratio from 0.1 to 90% by weight and preferably from 10 to 60% by weight of the entire preparation.

As the disintegrant may be contained one or more substances selected from the group consisting of 0.1-30% by weight, preferably 10-25% by weight of a lowly substituted hydroxypropylcellulose, 0.1-20% by weight, preferably 1-10% by weight of calcium carboxymethylcellulose, 0.1-10% by weight, preferably 2-5% by weight of hydrogenated oil and 0.1-20% by weight, preferably 2-10% by weight of talc.

The compounds of the general formula (I) in solid pharmaceutical preparations are so stable during long-term storage that stable pharmaceutical preparations such as tablets, capsules, granules and powders have become available.

Examples and a test example will be given below to describe the invention in particulars.

EXAMPLE 1

One gram of 2,6-dimethyl-4-(3-nitrophenyl)-1,4-dihydropyridine-3,5-dicarboxylic acid 3-(2-nitratoethyl) ester 5-(3-nitratopropyl) ester [the general formula (I): $R=-CH_2CH_2ONO_2$, $R^1=-CH_2CH_2CH_2ONO_2$, called Compound A hereinbelow], 27 g of lactose, 70 g of calcium hydrogen phosphate and 2 g of talc were uniformly blended and passed through a 42-mesh screen to give powders which were divided into 1-g packs.

EXAMPLE 2

Two grams of 2,6-dimethyl-4-(3-nitrophenyl)-1,4-dihydropyridine-3,5-dicarboxylic acid 3-(2-nitratopropyl) ester 5-(3-nitratopropyl) ester [the general formula (I): $R=-CH_2CH_2CH_2ONO_2$,

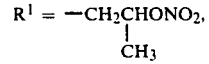

called Compound B hereinbelow], 30 g of corn starch, 59 g of mannit, 5 g of calcium carbonate and 4 g of lubriwax were uniformly blended and passed through a 42-mesh screen to give powders which were divided into 1-g packs.

EXAMPLE 3

Three grams of 2,6-dimethyl-4-(3-nitrophenyl)-1,4-dihydropyridine-3,5-dicarboxylic acid 3-(1-methyl-2-nitratoethyl) ester 5-(3-nitratopropyl) ester [the general formula (I): $R=-CH_2CH_2CH_2ONO_2$,

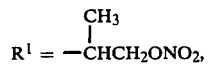

called Compound C hereinbelow], 25 g of corn starch, 62 g of lactose, 5 g of sodium hydrogen carbonate and 5 g of talc were uniformly blended and passed through a 42-mesh screen to give powders which were divided into 1-g packs.

EXAMPLE 4

Four grams of 2,6-dimethyl-4-(3-nitrophenyl)-1,4-dihydropyridine-3,5-dicarboxylic acid bis(2-nitratopropyl) ester [the general formula (I)

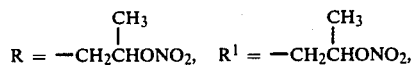

called Compound D hereinbelow], 74.5 g of corn starch, 10 g of a low substituted hydroxypropylcellulose (called LHPC hereinbelow) and 4 g of sodium carbonate were uniformly blended and then kneaded together with an appropriate amount of water employing 5 g of hydroxypropylcellulose (called HPC hereinbelow) as a binder followed by granulation in a basket granulator. The granules were dried and mixed with 2.5 g of hydrogenated oil to give granules which were divided into 1-g packs.

EXAMPLE 5

Five grams of Compound A, 36 g of lactose, 45 g of mannitol, 1 g of calcium carboxymethylcellulose (called CMC-Ca hereinbelow) and 2 g of sodium carbonate were uniformly blended and kneaded together with an appropriate amount of water by employing 5 g of HPC as a binder followed by drying and granulation. To the granules was added 6 g of talc followed by mixing to give granules which were divided into 1-g packs.

EXAMPLE 6

Six grams of Compound B, 20 g of corn starch, 36 g of lactose, 25 g of LHPC and 5 g of sodium carbonate were uniformly blended and kneaded together with an appropriate amount of water employing 5 g of HPC as a binder followed by drying and granulation. The granules were mixed with 3 g of hydrogenated oil to give granules which were divided into 1-g packs.

EXAMPLE 7

Twenty grams of Compound C, 12 g of lactose, 10 g of mannitol, 3 g of CMC-Ca and 40 g of calcium hydrogen phosphate were uniformly blended. From the blend were prepared wet granules employing 5 g of HPC as a binder in a conventional manner. The granules were dried, mixed with 10 g of talc and formed into granules. The resulting granules were tableted by the granule-compression method to give tablets each 8 mm in diameter and weighing 200 mg.

EXAMPLE 8

Fifteen grams of Compound D, 65.5 g of mannitol, 15 g of LHPC, 1 g of calcium carbonate and 3.5 g of lubriwax were uniformly blended and directly tableted into tablets each 7 mm in diameter and weighing 150 mg.

EXAMPLE 9

Thirty grams of Compound A, 45 g of corn starch, 5 g of CMC-Ca, 7 g of sodium carbonate and 5 g of HPC were uniformly blended and granulated by the dry granulation method. To the granules thus prepared were added 8 g of talc. The mixtures were tableted by the granule-compression method to give tablets each 6 mm in diameter and weighing 100 mg.

EXAMPLE 10

Ten grams of Compound B, 30 g of corn starch, 33 g of mannitol, 15 g of LHPC, 5 g of sodium hydrogen carbonate and 5 g of HPC were uniformly blended and kneaded together with an appropriate amount of water followed by mixing with 2 g of hydrogenated oil. The mixture was filled in gelatin capsules each containing 200 mg to give hard capsules.

EXAMPLE 11

Twenty grams of Compound C, 20 g of corn starch, 31 g of mannitol, 10 g of CMC-Ca, 10 g of sodium carbonate and 5 g of HPC were uniformly blended and kneaded together with an appropriate amount of water followed by drying and mixing with 4 g of talc. The mixture was filled in gelatin capsules each containing 100 mg to give hard capsules.

EXAMPLE 12

Twelve grams of Compound D, 48 g of mannitol, 20 g of LHPC 10 g of calcium hydrogen phosphate and 5 g of HPC were uniformly blended and formed into dry granules by the dry-granulation method. The granules were mixed with 5 g of hydrogenated oil. The mixture was filled in gelatin capsules each containing 240 mg to give hard capsules.

EXAMPLE 13

Ten grams of Compound B, 25 g of corn starch, 15 g of LHPC, 7 g of HPC and 40 g of calcium hydrogen phosphate were uniformly blended and kneaded together with an appropriate amount of water followed by mixing with 3 g of hydrogenated oil. The mixutre was formed by the granule-compression method into tablets each 8 mm in diameter and weighing 200 mg.

Test Example 1

Pharmaceutical preparations prepared in Examples 2, 6, 10 and 13, which were named Preparations 2, 6, 10 and 13, respectively were placed in 20-cc brown bottles which were closed and stored in a thermostat at 65°±2° C. for 14 days or at 50°±2° C. for 60 days. The resulting samples were analyzed by high performance liquid chromatography for said compounds. Comparison was made with the data prior to storage in the thermometer to calculate remaining ratio.

Remaining ratio (%) =

$$\frac{\text{Analytical value for said compound after aged at 65° C. ± 2° C. for 14 days or at 50° ± 2° C. for 60 days}}{\text{Analytical value for said compound prior to storage in the thermometer}} \times 100$$

Results are shown in Table 1.

The control preparation was the same preparation as in Example 6 except for omission of the sodium carbonate.

TABLE 1

| Preparation NO. | Remaining ratio of Compound B (%) | |
| --- | --- | --- |
| | 65° ± 2° C., 14 days | 50° ± 2° C., 60 days |
| 2 | 78.0 | 81.4 |
| 6 | 62.4 | 80.0 |
| 10 | 82.4 | 89.9 |
| 13 | 80.6 | 88.9 |
| control | 7.4 | 7.9 |

What is claimed is:

1. A solid pharmaceutical composition containing, as an active ingredient in an amount therapeutically effective in the treatment of circulatory disease, a 1,4-dihydropyridine derivative represented by the general formula

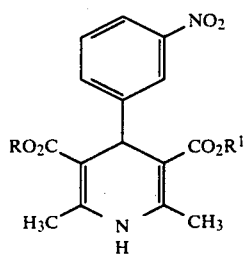

(I)

wherein R is a n-propyl group substituted at the 2- or 3-position with a nitrato group and R¹ is a 2-nitratoethyl group or 2-nitratoethyl substituted with a methyl group at the 1- or 2-position and, in an amount sufficient to stabilize said derivative, one or more compounds selected from the group consisting of sodium carbonate, sodium hydrogen carbonate, calcium carbonate and calcium hydrogen phosphate.

2. The composition according to claim 1 in which sodium carbonate, sodium hydrogen carbonate and/or calcium carbonate is incorporated in the range from 0.01 to 20 parts by weight per part by weight of the 1,4-dihydropyridine derivative (I).

3. The composition according to claim 1 in which calcium hydrogen phosphate is incorporated in the range from 0.01 to 100 parts by weight per part by weight of the 1,4-dihydropyridine derivative (I).

4. A method for stabilizing a solid pharmaceutical composition containing, as an active ingredient in an amount threapeutically effective in the treatment of circulatory disease, a 1,4-dihydropyridine derivative represented by the general formula

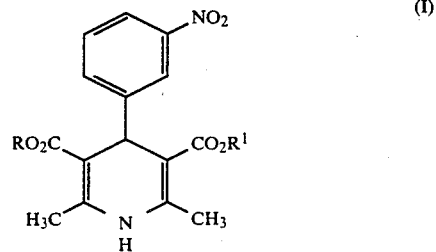

(I)

(wherein R is a n-propyl group substituted at the 2 or 3-position with a nitrato group and R¹ is a 2-nitratoethyl group which may be substituted with a methyl group at the 1- or 2-position) and pharmaceutical auxiliary agents which comprises incorporating in the composition, in an amount sufficient to stabilize said derivative, one or more compounds selected from the group consisting of sodium carbonate, sodium hydrogen carbonate, calcium carbonate and calcium hydrogen phosphate.

5. A composition in accordance with claim 1 additionally comprising at least one pharmaceutical auxiliary agent.

* * * * *